(12) United States Patent
Frisby (10) Patent No.: US 10,357,363 B2
(45) Date of Patent: Jul. 23, 2019

(54) TRANSCATHETER VALVE DELIVERY SYSTEM WITH CRIMPED PROSTHETIC HEART VALVE

(71) Applicant: Medtronic Vascular, Inc., Santa Rosa, CA (US)

(72) Inventor: Paraic Frisby, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 113 days.

(21) Appl. No.: 15/617,197

(22) Filed: Jun. 8, 2017

(65) Prior Publication Data
US 2017/0354498 A1 Dec. 14, 2017

Related U.S. Application Data

(60) Provisional application No. 62/347,955, filed on Jun. 9, 2016.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/95* (2013.01); *A61F 2/2433* (2013.01); *A61F 2/2439* (2013.01); *A61F 2002/9522* (2013.01); *A61F 2210/0014* (2013.01); *A61F 2230/0052* (2013.01); *A61F 2230/0054* (2013.01); *A61F 2250/0039* (2013.01)

(58) Field of Classification Search
CPC ................. A61F 2/2427–2439; A61F 2/95–97
See application file for complete search history.

(56) References Cited

U.S. PATENT DOCUMENTS

| | | | | |
|---|---|---|---|---|
| 4,470,157 A | * | 9/1984 | Love ..................... | A61F 2/2409 623/2.15 |
| 5,437,083 A | * | 8/1995 | Williams ................ | A61F 2/958 29/235 |
| 5,746,764 A | * | 5/1998 | Green ..................... | A61F 2/958 606/108 |
| 5,840,081 A | * | 11/1998 | Andersen .............. | A61F 2/2418 623/1.11 |
| 5,911,452 A | * | 6/1999 | Yan ......................... | A61F 2/958 29/282 |
| 5,920,975 A | * | 7/1999 | Morales ................. | A61F 2/958 29/282 |
| 5,957,949 A | * | 9/1999 | Leonhardt ............. | A61F 2/07 606/108 |
| 5,974,652 A | * | 11/1999 | Kimes ................... | A61F 2/958 29/282 |

(Continued)

*Primary Examiner* — Katrina M Stransky
*Assistant Examiner* — Brigid K Byrd (57) ABSTRACT

Stented prosthetic heart valve crimping tools and methods, and transcatheter delivery systems for delivering a crimped prosthetic heart valve. Methods of the present disclosure include crimping or compressing a stented prosthetic heart valve via spherical compression to a spherically compressed shape, and then delivering the so-shaped prosthesis to a target site. Delivery systems carrying a spherically-compressed prosthesis have a reduced length profile as compared to conventional, elongated configurations, providing increased maneuverability and positioning.

12 Claims, 10 Drawing Sheets

(56) References Cited

U.S. PATENT DOCUMENTS

| | | | | |
|---|---|---|---|---|
| 5,992,000 A * | 11/1999 | Humphrey | A61F 2/958 | 29/282 |
| 6,168,622 B1 * | 1/2001 | Mazzocchi | A61B 17/0057 | 606/200 |
| 6,325,815 B1 * | 12/2001 | Kusleika | A61B 17/221 | 606/200 |
| 6,425,916 B1 * | 7/2002 | Garrison | A61F 2/2418 | 623/1.26 |
| 6,605,102 B1 * | 8/2003 | Mazzocchi | A61B 17/12022 | 606/200 |
| 7,530,253 B2 * | 5/2009 | Spenser | A61F 2/2412 | 72/402 |
| 8,225,474 B2 * | 7/2012 | Arcand | A61F 2/958 | 29/272 |
| 9,021,670 B2 * | 5/2015 | Dale | A61F 2/2427 | 29/235 |
| 10,010,412 B2 * | 7/2018 | Taft | A61F 2/2418 | |
| 2001/0001890 A1 * | 5/2001 | Austin | A61F 2/95 | 29/282 |
| 2002/0062135 A1 * | 5/2002 | Mazzocchi | A61B 17/12022 | 606/200 |
| 2002/0138966 A1 * | 10/2002 | Motsenbocker | A61F 2/958 | 29/516 |
| 2003/0056360 A1 * | 3/2003 | Brown | A61F 2/958 | 29/516 |
| 2003/0070469 A1 * | 4/2003 | Kokish | A61F 2/958 | 72/402 |
| 2004/0128818 A1 * | 7/2004 | Motsenbocker | A61F 2/95 | 29/505 |
| 2005/0183259 A1 * | 8/2005 | Eidenschink | A61F 2/954 | 29/508 |
| 2005/0188525 A1 * | 9/2005 | Weber | A61F 2/958 | 29/508 |
| 2006/0213049 A1 * | 9/2006 | Serrano | B21D 39/048 | 29/508 |
| 2006/0265855 A1 * | 11/2006 | Stenzel | A61F 2/82 | 29/508 |
| 2006/0287717 A1 * | 12/2006 | Rowe | A61F 2/2412 | 623/2.11 |
| 2007/0006441 A1 * | 1/2007 | McNiven | A61F 2/958 | 29/508 |
| 2007/0129794 A1 * | 6/2007 | Realyvasquez | A61B 17/115 | 623/2.11 |
| 2007/0239254 A1 * | 10/2007 | Chia | A61F 2/2436 | 623/1.11 |
| 2008/0022504 A1 * | 1/2008 | Melsheimer | A61F 2/95 | 29/525 |
| 2008/0028594 A1 * | 2/2008 | Lafont | A61F 2/95 | 29/516 |
| 2008/0072653 A1 * | 3/2008 | Gillick | A61F 2/95 | 72/402 |
| 2008/0177381 A1 * | 7/2008 | Navia | A61F 2/2418 | 623/2.11 |
| 2009/0049675 A1 * | 2/2009 | Sokel | A61F 2/95 | 29/505 |
| 2009/0054976 A1 * | 2/2009 | Tuval | A61F 2/0095 | 623/2.11 |
| 2009/0299453 A1 * | 12/2009 | Arcand | A61F 2/958 | 623/1.11 |
| 2011/0301703 A1 * | 12/2011 | Glazier | A61F 2/2418 | 623/2.17 |
| 2012/0065729 A1 * | 3/2012 | Pintor | A61F 2/2412 | 623/2.11 |
| 2012/0083875 A1 * | 4/2012 | Johnson | A61F 2/2418 | 623/2.11 |
| 2013/0035759 A1 * | 2/2013 | Gross | A61F 2/2439 | 623/2.38 |
| 2013/0091688 A1 * | 4/2013 | Goetz | A61F 2/95 | 29/505 |
| 2013/0152658 A1 * | 6/2013 | Davis | A61F 2/95 | 72/370.12 |
| 2013/0197622 A1 * | 8/2013 | Mitra | A61L 31/145 | 623/1.15 |
| 2013/0310917 A1 * | 11/2013 | Richter | A61F 2/2427 | 623/1.12 |
| 2014/0243965 A1 * | 8/2014 | Benson | A61F 2/2418 | 623/2.18 |
| 2014/0309680 A1 * | 10/2014 | Fargahi | A61F 2/2433 | 606/191 |
| 2014/0324164 A1 * | 10/2014 | Gross | A61F 2/2409 | 623/2.37 |
| 2015/0320556 A1 * | 11/2015 | Levi | A61F 2/2427 | 623/2.11 |
| 2015/0336150 A1 * | 11/2015 | Peterson | A61F 2/2427 | 72/372 |
| 2017/0049566 A1 * | 2/2017 | Zeng | A61F 2/2418 | |
| 2017/0266003 A1 * | 9/2017 | Hammer | A61F 2/2418 | |
| 2018/0289486 A1 * | 10/2018 | Moll | A61F 2/2475 | |

* cited by examiner

TRANSCATHETER VALVE DELIVERY SYSTEM WITH CRIMPED PROSTHETIC HEART VALVE

CROSS-REFERENCE TO RELATED APPLICATIONS

This Non-Provisional Patent Application claims the benefit of the filing date of U.S. Provisional Patent Application Ser. No. 62/347,955, filed Jun. 9, 2016, entitled "Transcatheter Valve Delivery System with Crimped Prosthetic Heart Valve," the entire teachings of which are incorporated herein by reference.

BACKGROUND

The present disclosure relates to delivery systems for delivering a prosthetic heart valve. More particularly, it relates to transcatheter heart valve delivery systems carrying a crimped prosthetic heart.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With one type of stented prosthetic heart valve designs, the stent frame is formed to be self-expanding. The valved stent is crimped down to a desired size and held in that compressed state within a sheath or by other means for transluminal delivery. Retracting the sheath (or other release operation) from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety. Another type of valve stent can be initially provided in an expanded or uncrimped condition, then crimped or compressed about a balloon portion of a catheter. The balloon is subsequently inflated to expand and deploy the prosthetic heart valve.

The actual shape and configuration of any particular transcatheter prosthetic heart valve is dependent, at least to some extent, upon the valve being replaced or repaired (e.g., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the outer sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends; as the capsule (or other components of the delivery device) comes into atraumatic contact with the native anatomy, the native anatomy naturally assists in "forcing" the outer sheath (including the capsule) to the necessary shape.

Other anatomical-based constraints may be placed on the transcatheter delivery system, such as size and/or length. For example, when accessing certain valves via certain approach techniques, deployment of a conventionally-compressed and delivered prosthetic heart valve may be difficult due to anatomical space limitation (e.g., when accessing the mitral valve via trans-septal approach, limited space may be available in the left atrium for locating and manipulating the delivery system in effectuating prosthetic valve deployment). These anatomical constraints can be more difficult to address with larger stented prosthetic valve designs.

SUMMARY

The inventor of the present disclosure recognizes that a need exists for transcatheter prosthetic heart valve delivery systems and methods that overcome one or more of the above-mentioned problems.

Some aspects of the present disclosure are directed toward a method for loading a stented prosthetic heart valve to a delivery system. The method includes crimping the prosthesis via spherical compression, and locating the prosthesis in the compressed condition within an outer capsule of a delivery device. Spherical compression reduces a profile length of the outer capsule as compared to conventional techniques in which the stented prosthesis is crimped to, and held in, an elongated shape. Spherical compression can be accomplished with various tools or devices adapted to apply compressive forces on to the prosthesis in multiple directions, such as a collapsible bag or mesh including or connected to drawstrings or wires; tensioning the drawstrings or wires collapses the bag or mesh, in turn compressing a stented prosthesis located within the bag or mesh.

Other aspects of the present disclosure are directed toward methods of repairing a defective heart valve. The method includes crimping a stented prosthetic heart valve to a compressed condition via spherical compression, and loading the prosthesis, in the compressed condition, within a capsule of a delivery system. The delivery system is then manipulated to locate the capsule at the defective heart valve. The stented prosthetic heart valve is then released from the capsule, and deployed at the defective heart valve. In some embodiments, the defective heart valve is a mitral valve, and delivery system is manipulated through a trans-septal approach to the mitral valve. In other embodiments, a joint is formed in the capsule and the capsule is separated at the joint to release the prosthesis.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from, or in a direction away from the clinician. "Proximal" and "proximally" are a position near or in a direction toward the clinician. As used herein, with reference to an implanted valve prosthesis, the terms "distal" and "outflow" are understood to mean downstream to the direction of blood flow, and the terms "proximal" or "inflow" are understood to mean upstream to the direction of blood flow.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. In other embodiments, stent frames useful with systems and devices of the present disclosure have a balloon-expandable configuration as is known in the art. The stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1A:
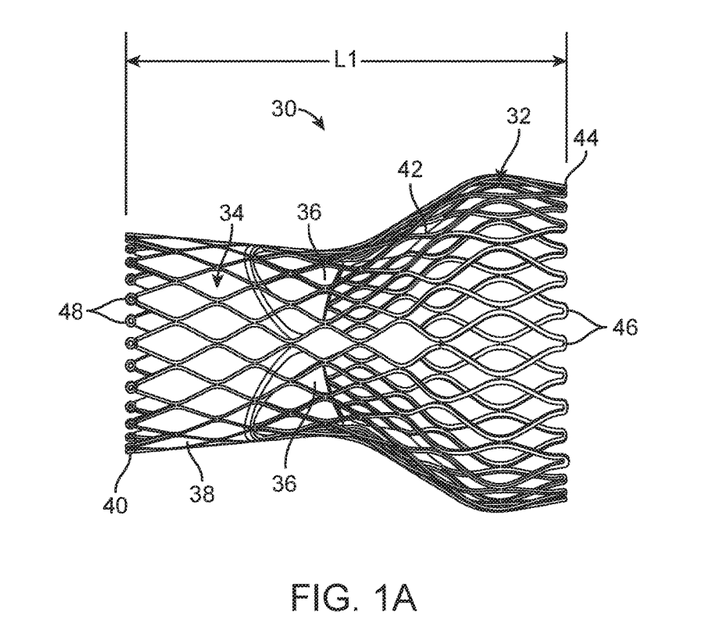
FIG. 1A is a side view of a stented prosthetic heart valve in a normal, expanded condition and useful with tools, systems and methods in accordance with principles of the present disclosure.
Figure 1B:
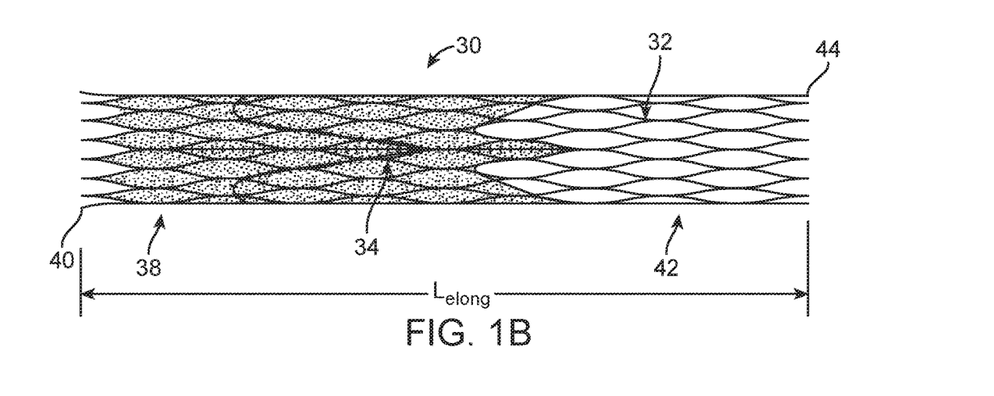
FIG. 1B is a side view of the stented prosthetic heart valve of FIG. 1A compressed to an elongated shape.

With the above understanding in mind, one simplified, non-limiting example of a stented prosthetic heart valve 30 useful with systems, devices and methods of the present disclosure is illustrated in FIG. 1A. As a point of reference, the prosthetic heart valve 30 is shown in a normal or expanded condition in the view of FIG. 1A; FIG. 1B illustrates an example of the prosthetic heart valve 30 in a compressed condition according to conventional delivery techniques as described below (e.g., when compressively retained within an outer catheter or sheath according to conventional practices). The prosthetic heart valve 30 includes a stent or stent frame 32 and a valve structure 34. The stent frame 32 can assume any of the forms mentioned above, and is generally constructed so as to be self-expandable from a compressed condition (such as the compressed condition of FIG. 1B or multiple other compressed conditions as described below) to the normal, expanded condition (FIG. 1A). In other embodiments, the stent frame 32 can have a balloon-expandable configuration.

The valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 can be formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve. In some constructions, the valve structure 34 can comprise two or three leaflets that are fastened together at enlarged lateral end regions to form commissural joints, with the unattached edges forming coaptation edges of the valve structure 34. The leaflets 36 can be fastened to a skirt that in turn is attached to the frame 32. The upper ends of the commissure points can define an inflow portion 38 corresponding to a first or inflow end 40 of the prosthesis 30. The opposite end of the valve can define an outflow portion 42 corresponding to a second or outflow end 44 of the prosthesis 30. As shown, the stent frame 32 can have a lattice or cell-like structure, and optionally forms or provides crowns 46 and/or eyelets 48 (or other shapes) at the outflow and inflow ends 40, 44.

Figure 2:
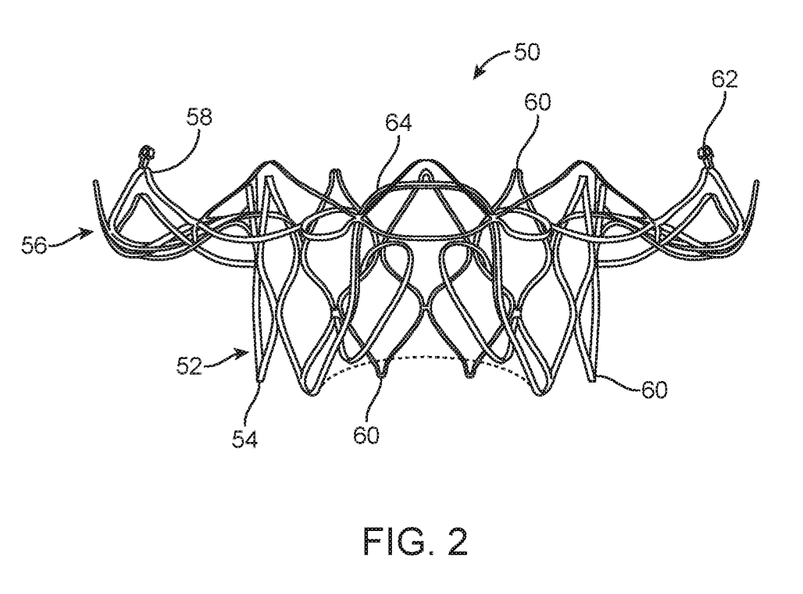
FIG. 2 is a side view of a portion of another stented prosthetic heart valve in a normal, expanded condition and useful with tools, systems, and methods of the present disclosure.

With the one exemplary construction of FIG. 1A, the prosthetic heart valve 30 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 2 illustrates a non-limiting example of a stent frame 50 portion of another prosthetic heart valve with which the systems, devices and methods of the present disclosure are useful. In the normal or expanded condition of FIG. 2, the stent frame 50 can be sized and shaped for mitral valve implantation. Though not shown, the valve structure attached to the stent frame 50 defines an outflow portion 52 arranged at a first or outflow end 54, and an inflow portion 56 arranged at a second or inflow end 58. As compared with the stent frame 32 of FIG. 1A, the inflow portion 56 can exhibit a more pronounced change in shape relative to the corresponding outflow portion 52. Regardless, the stent frame 50 can be forced and constrained to a compressed condition during delivery, and will self-expand to the natural condition of FIG. 2 upon removal of the constraining force(s). As reflected in FIG. 2, crowns 60 and/or eyelets 62 (or other shapes) optionally can be formed at one or both of the outflow and inflow ends 54, 58. Further, the stent frame 50 can optionally include or carry additional structural components, such as support arm(s) 64.

Regardless of an exact shape and structure of the stented prosthetic heart valve, conventional transcatheter delivery devices and methods crimp or collapse the stented prosthesis in a purely radial fashion. FIG. 1B represents the conventional radial-only crimping approach, and reflects that with purely radial crimp or collapse, a length of the prosthesis is naturally or inherently increased, generating an elongated shape. By way of further clarification, FIG. 1A identifies a length L1 of the prosthesis 30 in the normal or expanded condition, while FIG. 1B identifies a length $L_{elong}$ of the prosthesis 30 in a conventional, radial-only crimped condition (e.g., as commonly achieved using an iris-type or funnel-type crimping tool). The length $L_{elong}$ of the radial-only (or elongated) crimped condition is greater than the normal length L1.

Figure 3A:
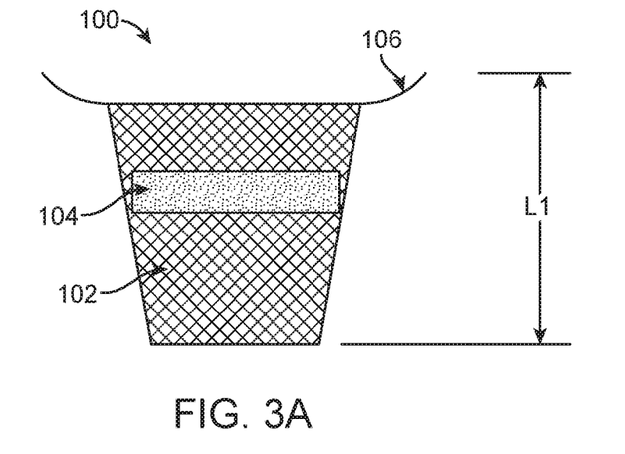
FIG. 3A is a simplified side view of a stented prosthetic heart valve.
Figure 3B:
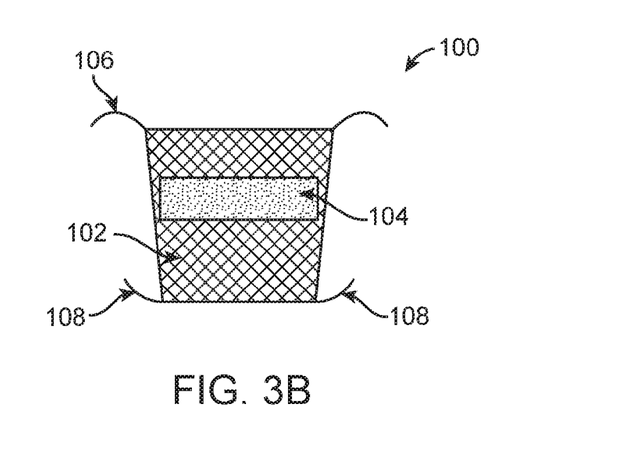
FIGS. 3B and 3C illustrate crimping of the stented prosthetic heart valve of FIG. 3A to a compressed condition via spherical compression in accordance with principles of the present disclosure.
Figure 3C:
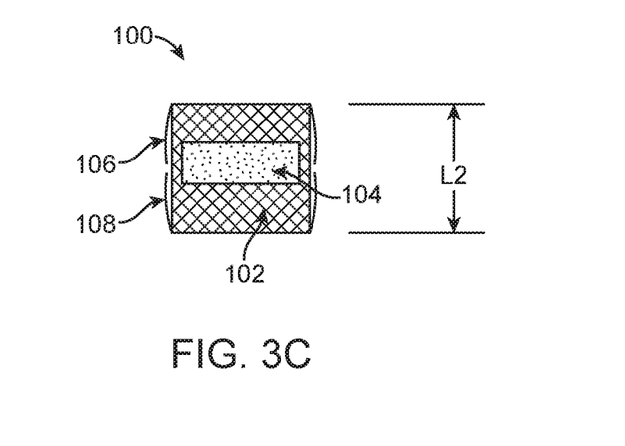

Against the above background, systems and methods in accordance with some aspects of the present disclosure entail crimping or collapsing the stented prosthetic heart valve via spherical compression for delivery to the target native valve. For example, FIG. 3A is a simplified representation of a stented prosthetic heart valve 100 in a normal or expanded condition and including a stent frame 102 maintaining a valve structure 104. With the systems and methods of the present disclosure, the prosthesis 100 is prepared for and loaded within a transcatheter delivery system (not shown) by collapsing or crimping the prosthesis 100 in multiple directions (not purely radial compression) via spherical compression as reflected by the progressions of FIGS. 3B and 3C. As schematically shown in the views, the stent frame 102 can include or develop strut segments 106, 108 at inflow and outflow ends before and/or during the compression process; with multi-directional (e.g., spherical) compression or crimping, the strut segments 106, 108 can collapse or fold around the valve structure 104. Alternatively, depending upon a shape of the stent frame 102 in the normal condition and the mechanisms or techniques utilized to effectuate multi-directional compression, the strut segments 106, 108 can become wrapped or collapsed in other directions. Regardless, in the collapsed condition of FIG. 3C, the prosthesis 100 has a spherical- or ball-like shape. In transitioning from the normal condition of FIG. 3A to the collapsed condition of FIG. 3C, a length of the prosthesis 100 is decreased. For example, the normal length L1 of the prosthesis 100 in FIG. 3A is shown as being greater than a collapsed length L2 in the collapsed condition of FIG. 3C.

Various tools and methods can be employed to provide spherical compression or collapsing of a stented prosthetic heart valve in accordance with principles of the present disclosure. For example, one non-limiting example is provided in FIG. 4A, and includes a flexible container 150 carrying two or more drawstrings 152 (or similar structures). The container 150 can assume various forms, such as a mesh or fabric bag or ball, and defines an internal volume 154. The container 150 is generally configured to be freely collapsible in all directions from the normal state of FIG. 4A to decrease the internal volume 154. The drawstrings 152 are interconnected to the container 150, and are operable to collapse the container 150 (e.g., the drawstrings 152 can be simultaneously pulled relative to the container 150).

Figure 4A:
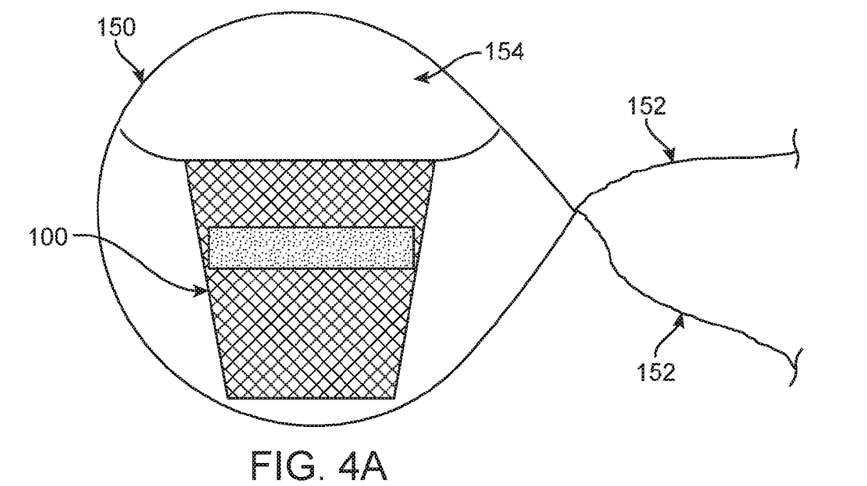
FIGS. 4A-4C are simplified views of a device and method for crimping a stented prosthetic heart valve to a compressed condition via spherical compression in accordance with principles of the present disclosure.
Figure 4B:
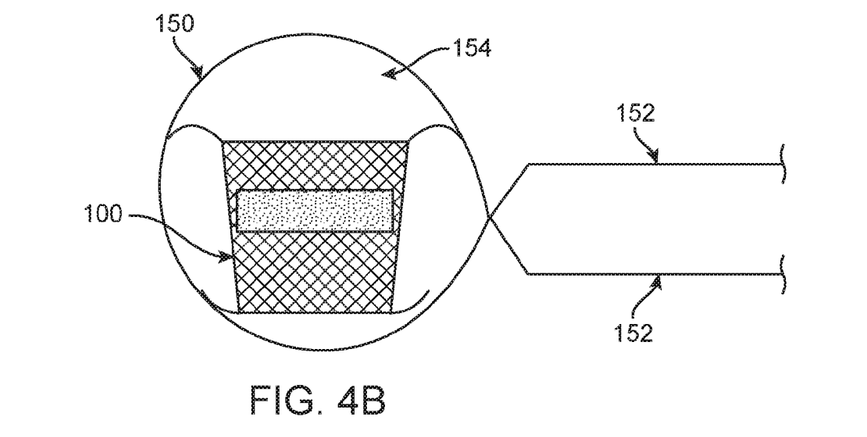
Figure 4C:
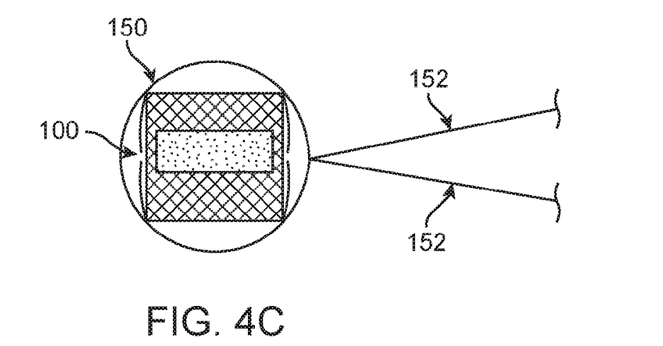

With the above construction, the internal volume 154 in the normal state of the container 150 is sized to receive the stented prosthetic heart valve 100 in the normal condition as shown in FIG. 4A (e.g., the container 150 receives and encompasses the prosthesis 100). The drawstrings 152 are then pulled (e.g., manually or using an actuator or other mechanism), causing the container 150 to collapse around the prosthesis 100, forcibly compressing the prosthesis 100 in multiple directions via spherical compression as reflected by the progression of FIG. 4B to FIG. 4C.

Figure 5A:
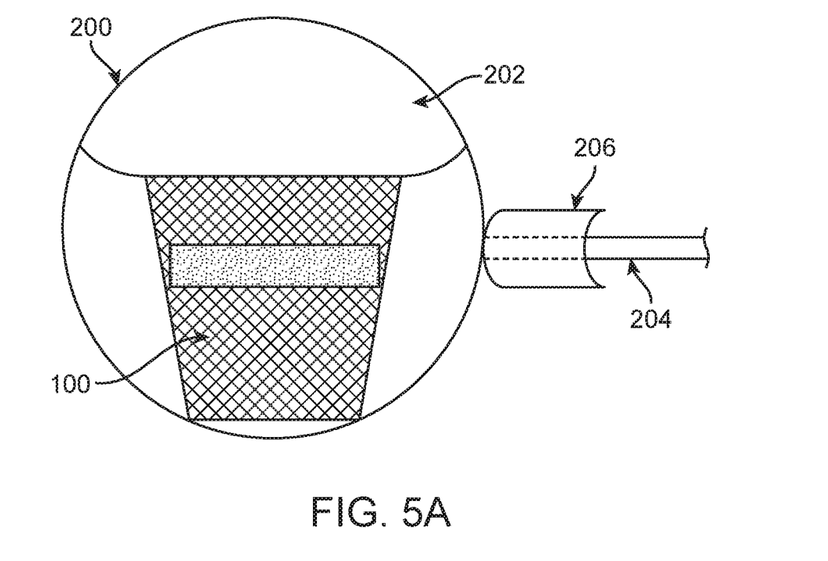
FIGS. 5A and 5B are simplified views of another device and method for crimping a stented prosthetic heart valve to a compressed condition via spherical compression in accordance with principles of the present disclosure.
Figure 5B:
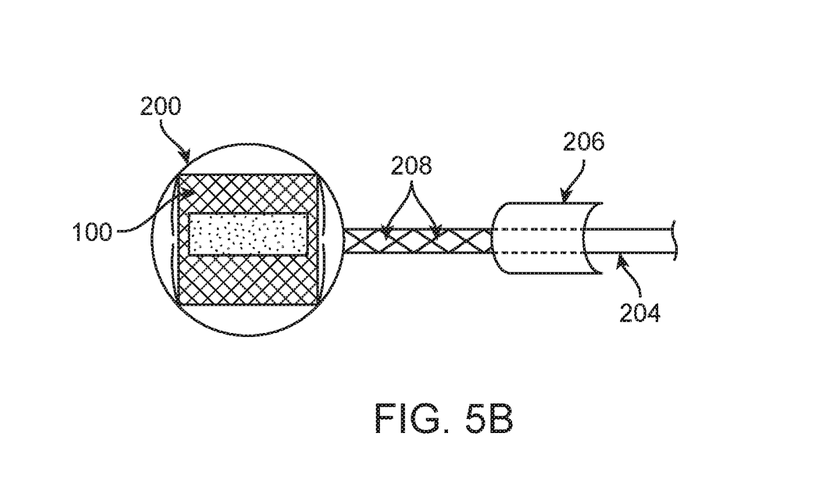

Another crimping system and method in accordance with principles of the present disclosure is shown in FIGS. 5A and 5B, and includes a collapsible hollow sphere or ball or container 200. In a normal state (FIG. 5A), the ball 200 forms an internal volume 202 sized to receive the stented prosthetic heart valve 100 in the normal or expanded condition. A shaft 204 is connected to the ball 200, and an actuator 206 is coupled to the shaft 204 (e.g., rotatably coupled, slidably coupled, etc.). Drawstrings or wires 208 (best seen in FIG. 5B) surround the ball 200, and are connected to the actuator 206. More particularly, movement of the actuator 206 relative to the shaft 204 (and thus the ball 200) tensions the drawing strings 208, in turn forcing the ball 200 to collapse in multiple directions. The actuator 206 can be manually articulated relative to the shaft 204; in other embodiments, a motor (not shown) or similar drive mechanism can automatically move the actuator 206. Regardless, tensioning of the drawstrings 208 causes the ball 200 to collapse around the prosthesis 100, forcibly compressing the prosthesis 100 in multiple directions via spherical compression as reflected by the progression from FIG. 5A to FIG. 5B. In some embodiments, the drawstrings 208 can wrap or wind about the shaft 204 with movement (e.g., rotation) of the actuator 206 as shown in FIG. 5B.

Figure 6A:
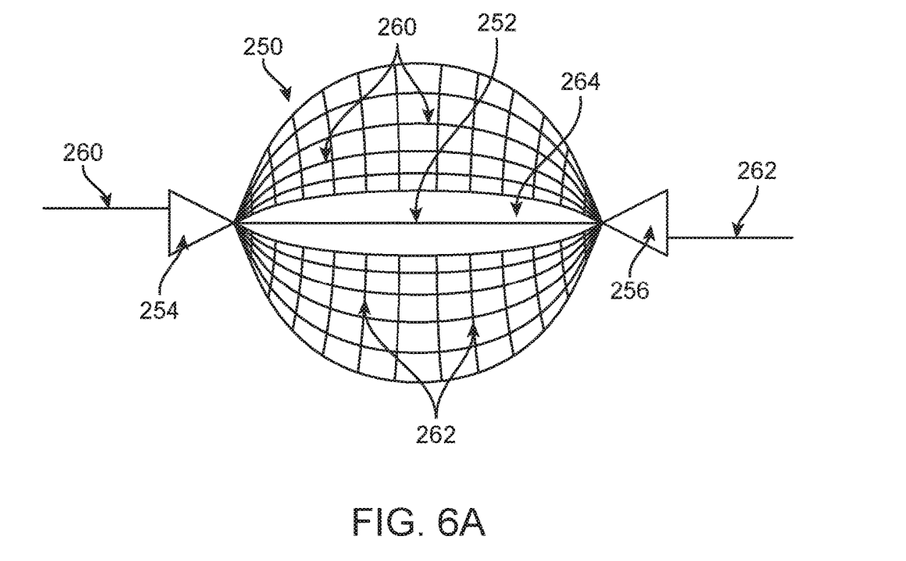
FIGS. 6A and 6B are simplified views of another device and method for crimping a stented prosthetic heart valve to a compressed condition via spherical compression in accordance with principles of the present disclosure.

Another crimping system and method in accordance with principles of the present disclosure is shown in FIG. 6A, and includes a spherical mesh 250, a rod or platform 252, a first actuator 254 and a second actuator 256. The spherical mesh 250 can assume various forms, and includes wires made of metal (e.g., Nitinol™), high strength polymer (e.g., polyethylene such as ultra-high molecular weight polyethylene), etc. The wires are arranged relative to a shape of the mesh 250 to define or include longitudinal wires 260 and latitudinal wires 262. The spherical mesh 250 is maintained over the rod 252 (i.e., the rod 252 extends within an internal volume of the spherical mesh 250), and forms a gap or discontinuity 264 through which a stented prosthetic heart valve (not shown in FIG. 6A) can be inserted into or removed from the confines of the spherical mesh 250.

Figure 6B:
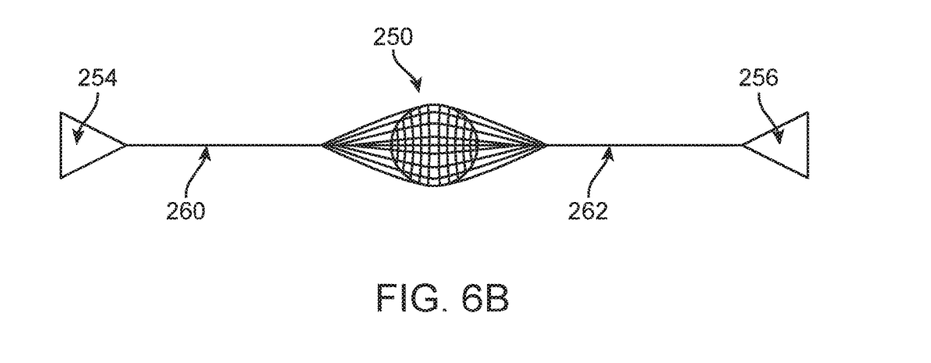

The actuators 254, 256 are slidably connected to the rod 252 and can each be or include a pulley or similar mechanism. The longitudinal wires 260 are connected to the first actuator 254, and the latitudinal wires 262 are connected to the second actuator 256. During use, a stented prosthetic heart valve (not shown in FIG. 6A) is placed within the spherical mesh 250, retained, for example, on the rod 252. The actuators 254, 256 are then activated (manually or automatically driven) in the directions identified by arrows in FIG. 6B, tensioning the longitudinal and latitudinal wires 260, 262, respectively. This action causes the mesh to contact onto itself, crimping down the stented prosthesis in multiple directions via spherical compression.

Figure 7A:
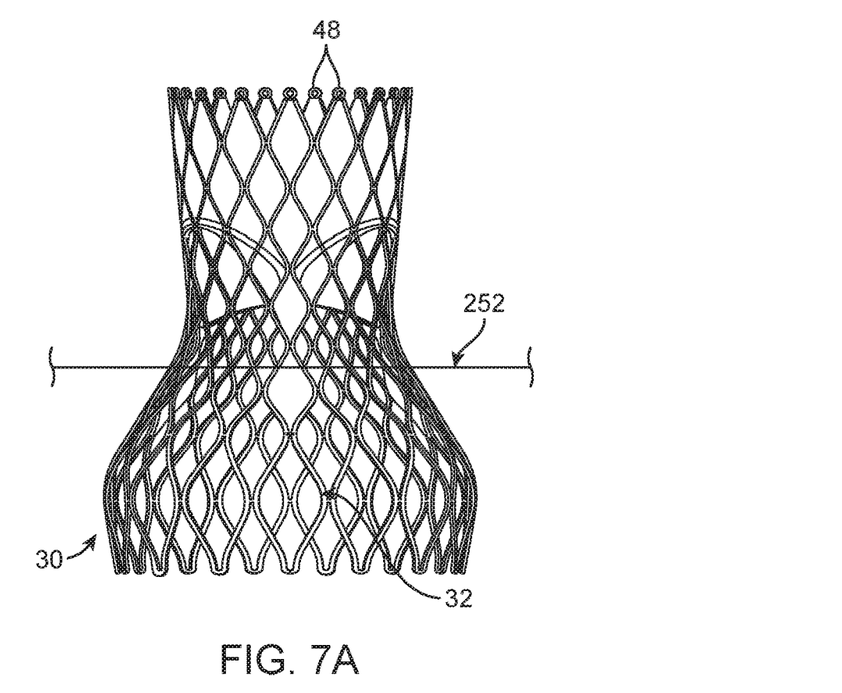
FIGS. 7A and 7B illustrate optional arrangements of a stented prosthetic heart valve relative to a component of the device of FIGS. 6A and 6B.
Figure 7B:
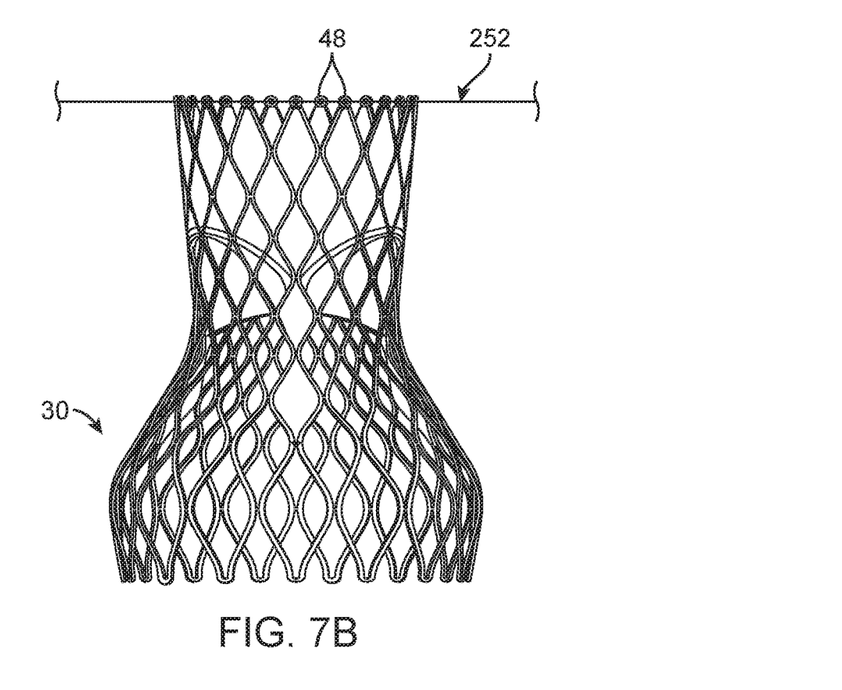

FIGS. 7A and 7B schematically illustrate non-limiting examples of how a stented prosthetic heart valve (e.g., the prosthesis 30) can be loaded on to the rod 252. In FIG. 7A, prosthesis is generally centered on the rod 252, with the rod 252 passing through opening or holes in the stent frame 32. In FIG. 7B, the rod 252 passes through one or more of the eyelets 48. Other assembly formats are also envisioned.

Figure 8A:
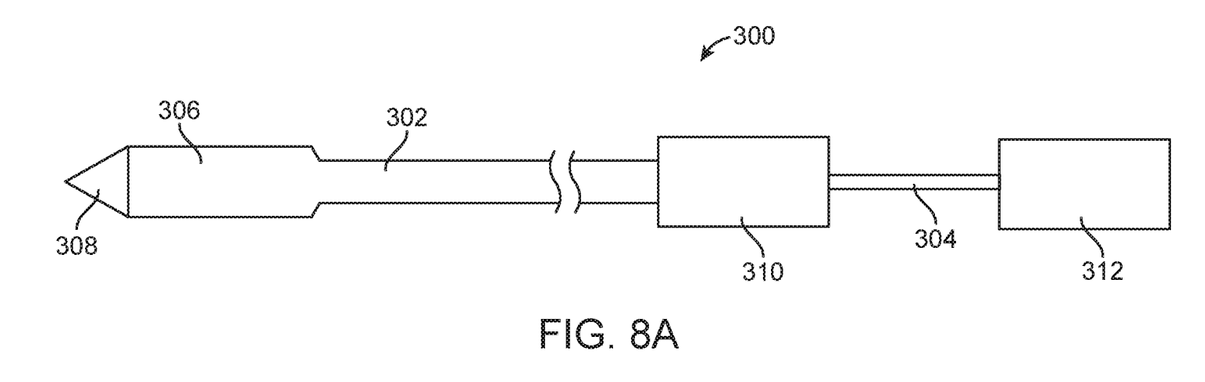
FIG. 8A is a simplified side view of a transcatheter delivery system.

Regardless of the mechanism or method employed for crimping or collapsing the stented prosthetic heart valve via spherical compression, the so-crimped prosthesis can be maintained and delivered to a target site using a delivery system configured to retain the crimped shape. One example of a delivery system 300 in accordance with principles of the present disclosure is schematically shown in FIG. 8A, and generally corresponds with conventional transcatheter prosthetic heart valve delivery systems by including an outer sheath 302 and an inner shaft assembly 304. The outer sheath 302 forms or is connected to a capsule, and is slidably disposed over the inner shaft assembly 304. Though hidden in the view of FIG. 8A, the inner shaft assembly 304 can form or include a valve retainer configured to selectively receive a corresponding features (e.g., posts or eyelets) provided with the prosthetic heart valve stent frame. The inner shaft assembly 304 includes or is attached to a tip 308. The outer sheath 302 is longitudinally slidable relative to the inner shaft assembly 304 (and vice-versa), for example via manipulation of corresponding actuators 310, 312 (that can be provided as part of a singular handle device).

Figure 8B:
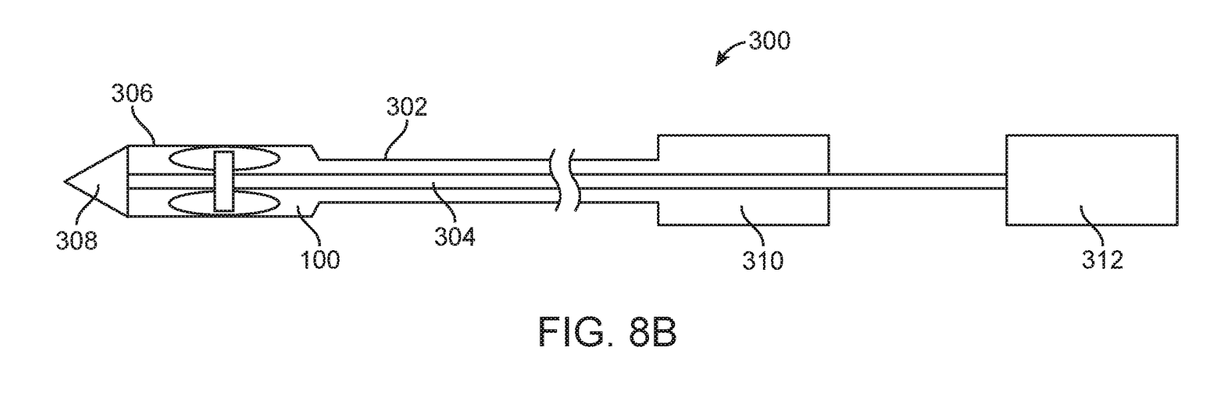
FIG. 8B is a simplified cross-sectional view of a stented prosthetic heart valve loaded to the delivery system of FIG. 8A in accordance with principles of the present disclosure.

FIG. 8B schematically illustrates the stented prosthetic heart valve 100 crimped via spherical compression to a crimped condition as described above and loaded to the delivery system 300. In the loaded or delivery arrangement of FIG. 8B, the prosthesis 100 is maintained in the crimped condition over the inner shaft assembly 304 by the capsule 306; where provided, the valve retainer (not shown) can promote a temporary connection between the prosthetic heart valve 100 and the inner shaft assembly 304. In the delivery condition of FIG. 8B, the prosthesis 100 is maintained in the spherically compressed condition, establishing a shorter working length for the capsule 306 as compared to conventional transcatheter heart valve delivery system designs. The prosthetic heart valve 100 can be deployed from the delivery system 300 by retracting the capsule 306 proximally relative to the inner shaft assembly 304 (and thus the prosthesis 100) and/or advancing the inner shaft assembly 304 (and thus the prosthesis 100) is distally relative to the capsule 306. As the capsule 306 is withdrawn from over the stented prosthetic heart valve 100 (or portions thereof), the prosthesis 100 is permitted to self-expand and release from the inner shaft assembly 304. The delivery system 300 can optionally include other components that assist or facilitate or control partial or complete deployment of the stented prosthetic heart valve 100 as are known the art.

Figure 9A:
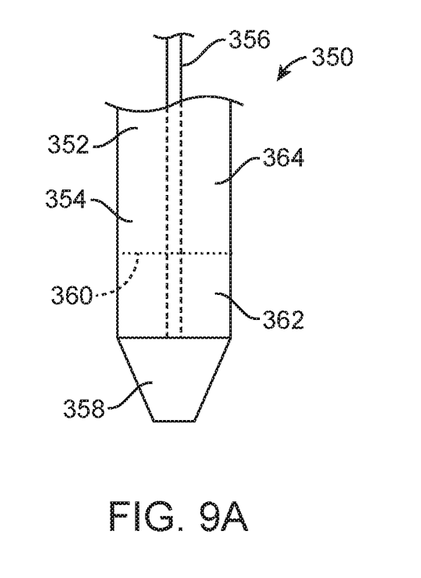
FIG. 9A is a simplified side view of a portion of another transcatheter delivery system in accordance with principles of the present disclosure.

Portions of another embodiment delivery system 350 in accordance with principles of the present disclosure are shown in simplified form in FIG. 9A, along with the stented prosthetic heart valve 100. The delivery system 350 can be akin to the delivery system 300 (FIG. 8A) described above, and includes an outer sheath 352 forming or connected to a capsule 354 and an inner shaft assembly 356 terminating at or connected to a tip 358. With the embodiment of FIG. 9A, a joint 360 is formed in the capsule 354, with the capsule 354 thus defining a distal segment 362 and a proximal segment 364 at opposite sides of the joint 360. While the capsule 354 initially is a continuous structure, the joint 360 is configured to promote or facilitate separation of the distal and proximal segments 362, 364 from one another. In this regard, the distal segment 362 is connected to the tip 358 (or other component of the inner shaft assembly 356) via an attachment mechanism (e.g., adhesive bond) that is more robust than the connection between the segments 362, 364 at the joint 360; similarly, the proximal segment 364 is more robustly connected to a remainder of the outer sheath 356 as compared to the connection established at the joint 360. With this construction, distal movement of the inner shaft assembly 356 (or portion thereof) relative to the outer sheath 352 and/or proximal movement of the outer sheath 352 relative to inner shaft assembly 356 causes the capsule 354 to separate at the joint 360.

Figure 9B:
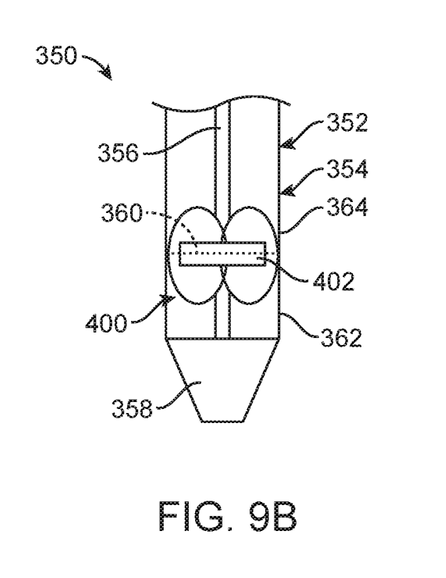
FIG. 9B is a simplified cross-sectional view of a stented prosthetic heart valve loaded to the delivery system of FIG. 9A in accordance with principles of the present disclosure.
Figure 9C:
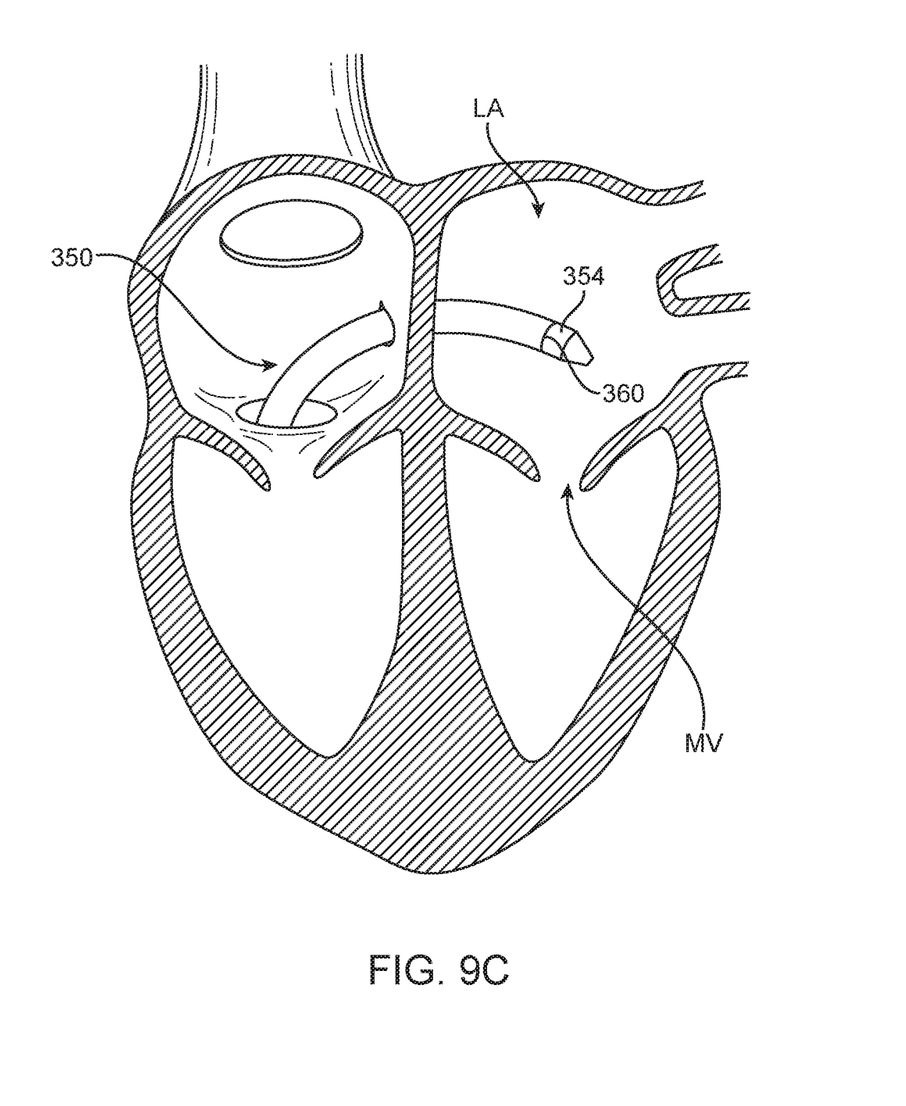
FIG. 9C illustrates use of the delivery system of FIGS. 9A and 9B in accessing a mitral valve via a trans-septal approach.

In some embodiments, the delivery system 350 is useful for delivering a stented prosthetic mitral valve to a native mitral valve via a trans-septal approach, although other prosthetic valve constructions, target sites, and delivery approaches are also acceptable. With reference to FIG. 9B, a stented prosthetic heart valve 400 is loaded to the delivery system 350 in a manner commensurate with the above descriptions, including the prosthesis 400 being crimped via spherical compression within the capsule 354. In this regard, inflow and outflow portions can be wrapped around a valve structure 402 of prosthesis 400 as represented in simplified form in FIG. 9B. Further, the stented prosthetic heart valve 400 can be arranged relative to the capsule 354 such that the valve structure 402 is generally aligned with the joint 360. The so-loaded delivery system 350 (including the prosthesis 400 constrained in the crimped or collapsed condition by the capsule 354) is then manipulated through the patient's vasculature toward a targeted heart valve. For example, FIG. 9C reflects an intermediate stage of one non-limiting delivery method in which the delivery system 350 has been manipulated through a trans-septal opening TS, locating the capsule 354 (and thus the prosthesis 400 (hidden) contained therein) within the left atrium LA for subsequent deployment of the prosthesis 400 at the native mitral valve MV. By crimping the prosthesis 400 to a spherically compressed condition, a length of the prosthesis 400 (and thus the length of the capsule 354) is relatively short (as compared to conventional transcatheter valve loading and delivery systems and techniques), and is thus readily manipulated within the left atrium LA and positioned at the native mitral valve MV.

Figure 9D:
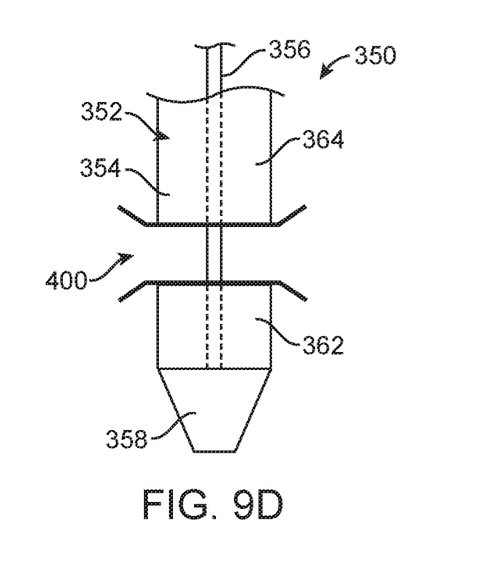
FIG. 9D is a simplified side view illustrating operation of the delivery system of FIGS. 9A and 9B to release the stented prosthetic heart valve.

The delivery system 350 is then further advanced to locate the capsule 354 at the mitral valve MV. In some non-limiting embodiments, the capsule 354 can be located such that the joint 360 is generally aligned with a plane of the mitral valve MV. The delivery system 350 is then actuated as in FIG. 9D so as to split the capsule 354 at the joint 360, for example by distally advancing the inner shaft assembly 356 relative to the outer sheath 352; this action advances the distal segment 362 relative to the stented prosthetic heart valve 400, allowing a portion of the prosthesis 400 to release from the delivery system 350 and self-expand (and shown in simplified form in FIG. 9D). The outer sheath 352 can then be proximally retracted relative to the inner shaft assembly 356, retracting the proximal segment 364 from over the prosthesis 400. When so retracted, the stented prosthetic heart valve 400 completely self-expands and releases from the delivery system 350.

The tools, systems and methods of the present disclosure provided a marked improvement over previous designs. Crimping or collapsing a stented prosthetic heart valve via spherical compression and delivering the prosthesis to a target site while maintaining the spherically compressed condition reduces a profile length of the prosthesis during delivery, and thus of the delivery system capsule utilized for transcatheter delivery (as compared to conventional crimping and delivery techniques providing for an elongated shape). The systems and methods of the present disclosure can be applied to other and future iterations of stented vascular valves, affording for the design and delivery of larger-than-conventional stented prosthetic valves.

Although the present disclosure has been described with reference to preferred embodiments, workers skilled in the art will recognize that changes can be made in form and detail without departing from the spirit and scope of the present disclosure. For example, while the devices and systems of the present disclosure have been described as being useful for delivering a stented prosthetic heart valve, a number of other implantable devices can be employed.

What is claimed is:

1. A method of loading a stented prosthetic heart valve to a transcatheter delivery system, the method comprising:
   crimping the stented prosthetic heart valve via spherical compression to a compressed condition; and
   locating the stented prosthetic heart valve in the compressed condition within an outer sheath of the delivery system.

2. The method of claim 1, wherein the step of crimping includes compressing the stented prosthetic heart valve from a normal, expanded condition to the compressed condition.

3. The method of claim 2, wherein the step of crimping includes applying a collapsing force onto the stented prosthetic heart valve in a plurality of directions.

4. The method of claim 3, wherein the stented prosthetic heart valve defines a longitudinal axis in the normal, expanded condition, and further wherein at least one of the plurality of directions is a non-radial direction relative to the longitudinal axis.

5. The method of claim 2, wherein the stented prosthetic heart valve includes a stent frame and a valve structure, and further wherein the valve structure is mounted to the stent frame so as to define an inflow section and outflow section along the stent frame at opposite sides of the valve structure, and even further wherein the compressed condition includes at least one of the inflow and outflow sections wrapped about the valve structure.

6. The method of claim 5, wherein the compressed condition includes both of the inflow and outflow sections wrapped about the valve structure.

7. The method of claim 1, wherein the step of crimping includes:
   placing the stented prosthetic heart valve, in a normal condition, into a collapsible bag; and
   forcibly collapsing the bag to compress the stented prosthetic heart valve.

8. The method of claim 7, wherein the step of collapsing includes tensioning a plurality of drawstrings connected to the bag.

9. The method of claim 7, wherein the step of collapsing includes manipulating an actuator connected to the bag.

10. The method of claim 7, wherein the bag is a mesh material defining longitudinal and latitudinal wires.

11. The method of claim 10, wherein the step of collapsing includes tensioning the longitudinal wires with a first actuator and tensioning the latitudinal wires with a second actuator.

12. The method of claim 1, wherein the compressed condition includes the stented prosthetic heart valve assuming a spherically compressed shape.

\* \* \* \* \*